United States Patent [19]

Anspach, Jr.

[11] Patent Number: 5,102,421

[45] Date of Patent: Apr. 7, 1992

[54] SUTURE ANCHOR AND METHOD OF FORMING

[75] Inventor: William E. Anspach, Jr., 1349 S. Killian Dr., Lake Park, Fla. 33403

[73] Assignees: Wm. E. Anpach, III; Amy A. McGarrity; Thos. D. Anspach, all of Lake Park, Fla.

[21] Appl. No.: 537,588

[22] Filed: Jun. 14, 1990

[51] Int. Cl.$^5$ .................. A61B 17/00; A61F 5/04
[52] U.S. Cl. .................. 606/232; 606/60; 606/72; 606/73
[58] Field of Search ........... 606/232, 233, 222, 223, 606/224, 225, 226, 227, 184, 167, 185, 63, 64, 65, 67, 95, 104, 187, 60, 62, 72-75, 101; 623/13, 187

[56] References Cited

U.S. PATENT DOCUMENTS

| | | | |
|---|---|---|---|
| 722,105 | 4/1903 | Hervey | 606/222 |
| 1,105,105 | 7/1914 | Sherman | 606/73 |
| 2,121,193 | 6/1938 | Hanicke | 606/65 |
| 3,003,155 | 10/1961 | Mielzynski | 606/187 |
| 3,123,077 | 4/1964 | Alcamo | 606/228 |
| 4,532,926 | 8/1985 | O'Holla | 606/232 |
| 4,628,923 | 12/1986 | Medoff | 606/65 |
| 4,632,100 | 12/1986 | Somers et al. | 606/79 |
| 4,738,255 | 4/1988 | Goble et al. | 623/16 |
| 4,776,528 | 10/1988 | Frey et al. | 606/72 |
| 4,790,303 | 12/1988 | Steffee | 606/86 |
| 4,796,612 | 1/1989 | Reese | 606/72 |
| 4,940,467 | 9/1990 | Tronzo | 606/73 |
| 4,963,144 | 10/1990 | Huene | 606/104 |
| 4,968,318 | 12/1990 | Ga Harna | 606/232 |

Primary Examiner—Randall L. Green
Assistant Examiner—K. Reichie
Attorney, Agent, or Firm—Jack N. McCarthy

[57] ABSTRACT

A suture anchor, or rivet, for fixing one end of a suture in a bone has a forward and formed of a plurality of truncated cones positioned in line behind a cone with a cylindrical member extending from the last truncated cone forming the rear end; a plurality of spiral grooves extend through the outer surfaces of the truncated cone and cone for spirally inserting the anchor, the spiral grooves forming serrations therebetween to prevent the suture anchor from being withdrawn from a bone into which it has been driven. An impact tool is used having a hole in the end to receive and engage the cylindrical member of the suture anchor.

24 Claims, 1 Drawing Sheet

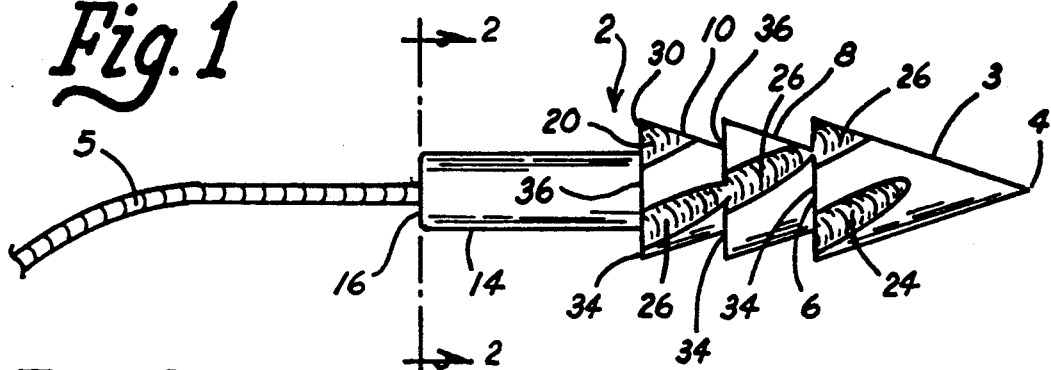
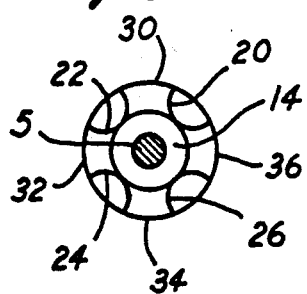
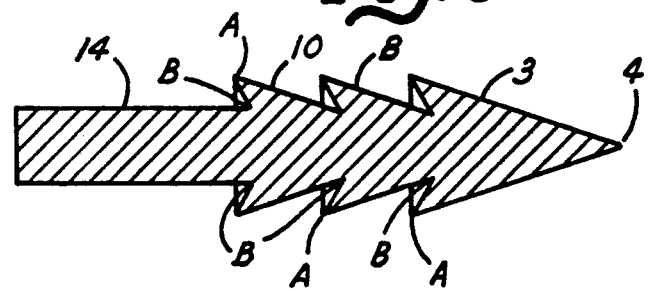
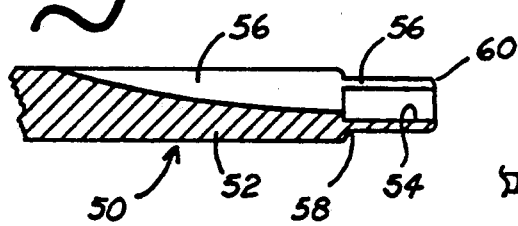
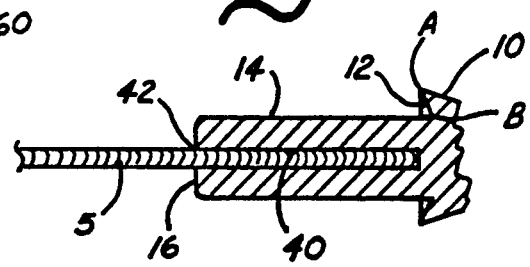
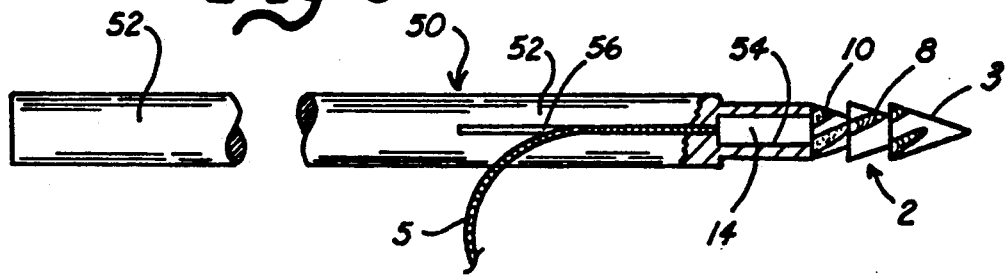

SUTURE ANCHOR AND METHOD OF FORMING

DESCRIPTION

1. Technical Field

This invention relates to an apparatus for attaching sutures to bone, and to a method for making the same.

2. Background Art

It is frequently necessary for a surgeon to attach sutures to bone. These sutures are then generally passed through ligaments or tendons to hold them in place. As the use of grafted tendons becomes more common, their use is more frequent. The usual method of attaching a suture to bone is to drill a pair of holes a short distance apart, thread the suture down into one hole and back out the other; thus, using the short bone bridge between the holes as the structural attachment. This method is frequently difficult in deep wounds where access to instruments is limited, and the bone stock may be fragile enough that the suture breaks through the bridge between the holes. This method is also time consuming.

Patents uncovered which set forth related devices are U.S. Pat. No. 3,123,077 to Alcamo; U.S. Pat. No. 4,049,974 to Freedland; U.S. Pat. No. 4,738,255 to Goble et al; U.S. Pat. No. 4,741,330 to Hayhurst; and U.S. Pat. No. 4,790,303 to Steffee.

DISCLOSURE OF INVENTION

It is an object of this invention to provide a suture anchor, or rivet, having a sharply pointed end so that it is capable of being driven into a bone by itself.

Another object of this invention is to provide a suture anchor, or rivet, consisting of a rod at one end to which a suture can be attached, while at the other end a conical tip is attached to the rod by a truncated conical member, the base of said conical tip and truncated conical member being substantially the same; spiral grooves extend along the length of the truncated conical member and into said conical tip.

A further object of this invention is to provide an elongated suture anchor, or rivet, having three radially extending flanges at the forward end having the same outer diameter and a cylindrical member at the rearward end having a smaller diameter, the two radially extending rear flanges having a forward surface tapering downwardly and forwardly from its outer edge to the rear surface of the flange in front of it, the radial extending front flange having a forward face tapering downwardly and forwardly from its outer edge to form a cone; the two radially extending forward flanges having a rear base surface tapering downwardly and forwardly from its outer edge to meet the cooperating forward surface of the flange behind it, the radial extending rear flange having a rear base surface tapering downwardly and forwardly from its outer edge to meet the forward end of the cylindrical member behind it; spiral grooves extend through said three radially extending flanges, said spiral grooves forming wide-ended serrations in each radially extending flange acting as barbs to prevent the suture anchor, or rivet, from being withdrawn.

Another object of the invention is to provide a suture anchor, or rivet, not requiring any canulas, undercutting drills, or complex threading and driving devices for its implantation. The suture anchor, or rivet, has a sharp point which can be driven into a bone directly or through a very small drill hole, such as one of 0.080 of an inch if the bone is relatively hard.

A further object of this invention is to provide an impact tool for driving said suture anchor, or rivet, into a bone, said impact tool having an opening in its impacting end to receive a cylindrical portion of the suture anchor, or rivet, the bottom of said opening presenting a surface to contact the end of the cylindrical portion of the suture anchor, or rivet, to drive it in place; a groove extends down the side of said impact tool into said opening for receiving the attached suture from said suture anchor, or rivet, so that the suture can be held by the surgeon when the impact tool is used.

Another object of this invention is to provide a method of forming a suture anchor, or rivet, wherein the tip of the anchor to be driven into a bone is formed with a conical tip with a truncated conical member at the rear end thereof, a cylindrical member is then formed behind the truncated conical member; a plurality of spiral grooves are then formed extending the length of the truncated conical member and rear portion of the conical tip causing the suture anchor, or rivet, to rotate as it is driven into place; an opening is provided in the cylindrical member for attaching a suture thereto.

BRIEF DESCRIPTION OF DRAWINGS

FIG. 1 is a side view of the suture anchor, or rivet, with a suture affixed thereto;

FIG. 2 is a figure taken on the line 2—2 of FIG. 1;

FIG. 3 is a longitudinal sectional view of the suture anchor, or rivet, before a suture holding opening has been placed therein and before the spiral grooves have been placed therein;

FIG. 4 is a fragmentary sectional view showing the rear cylindrical extension member with an opening drilled therein having a suture permanently fixed therein;

FIG. 5 is a figure showing the impact tool for driving said suture anchor, or rivet, into a bone, with a suture anchor, or rivet, in place with an attached suture;

FIG. 6 is a fragmentary sectional view showing the driving end of the impact tool.

BEST MODE FOR CARRYING OUT THE INVENTION

A suture anchor, or rivet, 2 for a suture 5 is formed having a forward conical member 3 having a pointed forward end, or tip, 4 and a rear base 6 with two truncated conical members 8 and 10 connected axially in line to the base of the forward conical member 3. Each truncated conical member 8 and 10 has its smaller top connected, respectively, to the larger base of the conical member 3 or truncated conical member 8 in front of it. The base 12 of the rear truncated conical member 10 has a rear cylindrical extension member 14 attached axially in line thereto for providing (1) a suture attachment; and (2) an impact surface 16 to drive the suture anchor, or rivet, 2 in place in a bone, to be hereinafter described.

Each base of conical member 3 and truncated conical members 8 and 10 has the same diameter, and each top of truncated conical members 8 and 10 has the same diameter where it connects to the base in front of it. Said rear cylindrical extension member 14 has a diameter equal to each top of truncated conical members 8 and 10. Further, each annular exposed portion of the base of conical member 3 and truncated conical members 8 and 10 is formed as an inwardly tapered surface extending from its outer edge A forwardly to its inner edge B where it meets the top of a connected truncated conical member 8 or 10, or cylindrical extension member 14.

Spiral grooves 20, 22, 24 and 26 are spaced around the truncated conical members 10, 8 and conical member 3 and extend along the conical members as continuous grooves. Said grooves 20, 22, 24 and 26 have a depth extending to the outer diameter of the cylindrical extension member 14 and the tops of the truncated conical members 10 and 8. Said spiral grooves 20, 22, 24 and 26 form a plurality of wide-ended serrations 30, 32, 34 and 36 therebetween, around each base of truncated conical members 10 and 8 and conical member 3, and a longitudinally off-set spiral series of wide-ended serrations 30, 32, 34 and 36 along the length of truncated conical members 10 and 8 and along the rear portion of conical member 3. The spiral series of wide-ended serrations 30, 32, 34 and 36 cause the suture anchor, or rivet, 2 to rotate as it is impacted into a bone. Said wide-ended serrations act to prevent said suture anchor, or rivet, 2 from being withdrawn during its normal holding function. The off-set spiral position of the wide-ended serrations 30, 32, 34 and 36 aid in preventing withdrawal.

The cylindrical extension member 14 has a drilled hole 40 therein for holding one end of a suture 5 which is to be fixed to a bone. If the material of the suture anchor 1 is a metal, such as stainless steel, the suture 5 can be held in the drilled hole 40 by swaging; if the material of the suture anchor 2 is an implantable plastic, such as UDEL POLYSOLFONE ®, the suture 5 can be held by thermal working of the anchor wall. Other known means of affixing a suture 5 can be used. The end of the drilled hole 40 is chamfered (or rounded) at 42 to prevent unnecessary stress on a suture 5 fixed in said drilled hole 40. When the suture anchor, or rivet, 2 is driven into a bone, the suture anchor, or rivet, 2 is completely buried with its rear end 16 flush with the bone surface so that only the suture 5 protrudes.

FIG. 3 shows the suture anchor, or rivet, 2 partially completed, with the integrated forward end formed of two cone frustums 10 and 8, and a cone 3; with the exposed annular ends of the bases thereof tapered inwardly and forwardly. The cylindrical member 14 is shown without its receiving hole 40. When the spiral grooves 20, 22, 24 and 26 are placed around the cone frustums 10 and 8, and cone 3, they form the wide-ended serrations 30, 32, 34 and 36 therebetween, referred to hereinbefore. FIG. 3 shows that each wide-ended serration will project backwardly from the pointed forward end, or tip, 4 and be provided with a degree of resiliency at the rear end.

An impact tool 50 comprises a rod 52 having a hole 54 in one end thereof to receive the cylindrical extension member 14 of suture anchor, or rivet, 2. A thin groove, or slit, 56 extends through the side of the one end of the rod 52 into hole 54 to below the center thereof. The thin groove, or slit, 56 extends into the rod 52 to accommodate the suture 5 extending from the end of the cylindrical extension member 14 when the cylindrical extension member 14 is being placed in a hole 54. The depth of the hole 54 is less than the length of the cylindrical extension member 14 so that the bottom of the hole 54 will drive against the end of the cylindrical extension member 14 when the suture anchor, or rivet, 2 is being implanted. The end of the rod 52 is reduced at 58 and the annular end is tapered like the annular exposed portion of the base of cone frustum 10.

In a construction made, the suture anchor 2 was approximately 0.625 inches long, the flanged front end was approximately 0.375 inches long, and the rear cylindrical member 14 was approximately 0.25 inches long.

While the principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

I claim:

1. A suture anchor for driving into a bone comprising a forward end having a first cone, said first cone having a pointed end for driving into a bone and a base with an outer surface extending therebetween, at least one truncated cone positioned behind said first cone, said at least one truncated cone having a base and an opposite end surface of smaller diameter with an outer surface extending therebetween, said at least one truncated cone having its end surface of smaller diameter fixed to the base of the first cone, a rearwardly extending member extends from the base of said at least one truncated cone, and a plurality of spiral grooves on said at least one truncated cone and on said first cone extending through the outer surfaces of said at least one truncated cone and first cone for causing said suture anchor to rotate as it is driven into place, said rearwardly extending member having means for attaching a suture thereto.

2. A combination as set forth in claim 1 wherein said at least one truncated cone includes a plurality of said truncated cones coaxially positioned in line behind said first cone, each truncated cone except for the forwardmost truncated cone having its end surface fixed to the base of the truncated cone forwardly adjacent thereof, said forwardmost truncated cone having its end surface fixed to the base of the first cone, and said rearwardly extending member extends from the base of the rearmost truncated cone.

3. A combination as set forth in claim 2 wherein said base of said first cone and said bases of said truncated cones have the same diameter, said opposite end surfaces of smaller diameter of said truncated cones having the same outer diameter, said grooves having a depth extending to the outer diameter of said opposite end surfaces of smaller diameter.

4. A combination as set forth in claim 1 wherein the base of said first cone has an annular exposed portion around the opposite end surface of smaller diameter of said at least one truncated cone where it is fixed to the base, said annular exposed portion being tapered inwardly and forwardly towards the opposite end surface of smaller diameter of said at least one truncated cone.

5. A combination as set forth in claim 4 wherein the base of said at least one truncated cone has an annular exposed portion around the rearwardly extending member where it is fixed to the base, said annular exposed portion being tapered inwardly and forwardly towards the rearwardly extending member.

6. A combination as set forth in claim 5 wherein said spiral grooves have elongated serrations (30, 32, 34 and 36) therebetween on said at least one truncated cone and first cone, each serration having an end projecting backwardly (as at A).

7. A combination as set forth in claim 6 wherein said serrations extend along the length of said at least one truncated cone and along the rear portion of the first cone.

8. A combination as set forth in claim 1 wherein said rearwardly extending member is a cylindrical member, said spiral grooves extend to a depth to be aligned with the outer surface of said rearwardly extending cylindrical member.

9. A combination as set forth in claim 1 wherein said rearwardly extending member has a rear end, and said suture attaching means includes hole which extends into the rear end of said rearwardly extending member, and further comprising a suture, one end of said suture being fixed in said hole.

10. A combination as set forth in claim 9 wherein the hole where the suture protrudes from the rear end of the rearwardly extending member is chamfered to prevent stress being placed on the suture at that chamfered location.

11. A combination as set forth in claim 1 wherein said spiral grooves on said at least one truncated cone and said spiral grooves on said first cone extend as continuous grooves from said at least one truncated cone to said first cone.

12. A combination as set forth in claim 1 wherein each of said plurality of spiral grooves extends the length of said at least one truncated cone and rear portion of the first cone.

13. A combination as set forth in claim 1 wherein said plurality of spiral grooves includes four spaced spiral grooves on said first cone.

14. A method of making a suture anchor for driving into a bone comprising the steps of:
(1) forming a first cone having a pointed end, a base, and an outer bone engaging surface therebetween;
(2) forming a truncated cone having a small end smaller than the base of the first cone, a base, and an outer surface therebetween with its small end connected to the base of said first cone leaving an annular outer portion of the base of the first cone not covered;
(3) forming a rearwardly extending member connected to the base of said truncated cone leaving an outer portion of the base of the truncated cone not covered; and
(4) forming spiral grooves on said truncated cone and on said first cone extending through the outer surface of said truncated cone and said first cone.

15. A method as set forth in claim 14 including the steps of:
(5) forming the annular outer portion of the base of the first cone taperd inwardly and forwardly; and
(6) forming the outer portion of the base of the truncated cone tapered inwardly and forwardly.

16. A method as set forth in claim 15 including in step (4) forming elongated serrations between said spiral grooves with each serration having a wide-end projecting rearwardly.

17. A method as set forth in claim 14 including:
in step (3) forming a cylindrical rearwardly extending member; and
step (5) forming said spiral grooves to a depth to be aligned with the outer surface of said cylindrical rearwardly extending member.

18. A method as set forth in claim 14 including:
in step (4) forming spiral grooves of said truncated cone and said first cone as continuous grooves from said truncated cone to said first cone.

19. A method as set forth in claim 14 including in step (4) forming four spaced spiral grooves.

20. A suture anchor for driving into a bone comprising a forward end having three radially extending flange means for engaging bone and a rear end defining a cylindrical member, said three radially extending bone engaging flange means having forward surfaces and rear surfaces with an outer periphery, the two rearmost radially extending flange means each having its forward surface tapering inwardly and forwardly from the outer periphery of the rear surface to the rear surface of the flange means in front of it, the forwardmost radially extending flange means having said forward surface tapering inwardly and forwardly from the outer periphery of the rear surface to form said forward end in a point for driving into a bone, the rear surface of said two forwardmost radially extending flange means tapering inwardly and forwardly from its outer periphery to the cooperating forward surface of the flange means behind it, the rear surface of said rearmost radially extending flange means tapering inwardly and forwardly from its outer periphery to meet the forward end of the cylindrical member behind it, spiral grooves on said three radially extending flange means which extends through the forward surfaces and rear surfaces of said three radially extending flange means, said cylindrical member having means for attaching a suture thereto.

21. A combination as set forth in claim 20 wherein said spiral grooves form wide-end serrations around each radially extending bone engaging flange means, said wide-end serrations being off-set axially between adjacent radially extending flange means.

22. A combination as set forth in claim 20 wherein said suture anchor is one piece.

23. A combination as set forth in claim 20 wherein said cylindrical member has a rearward end impact surface to drive the suture anchor in place.

24. A combination as set forth in claim 23 wherein said impact surface is annular.

* * * * *